United States Patent
Miyajima et al.

(10) Patent No.: US 10,130,336 B2
(45) Date of Patent: Nov. 20, 2018

(54) ULTRASOUND PROBE THAT EXHAUSTS HEAT VIA INFRARED-RADIATIVE HEAT TRANSFER

(75) Inventors: Yasuo Miyajima, Utsunomiya (JP); Hironobu Hongou, Otawara (JP); Toru Hirano, Otawara (JP); Isao Uchiumi, Nasushiobara (JP); Nobuyuki Iwama, Nasushiobara (JP); Masaaki Ishitsuka, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 478 days.

(21) Appl. No.: 13/982,062

(22) PCT Filed: Aug. 21, 2012

(86) PCT No.: PCT/JP2012/071070
§ 371 (c)(1),
(2), (4) Date: Jul. 26, 2013

(87) PCT Pub. No.: WO2013/031580
PCT Pub. Date: Mar. 7, 2013

(65) Prior Publication Data
US 2013/0303918 A1 Nov. 14, 2013

(30) Foreign Application Priority Data
Sep. 1, 2011 (JP) .................... 2011-190666

(51) Int. Cl.
*A61B 8/14* (2006.01)
*A61B 8/00* (2006.01)
*A61B 8/06* (2006.01)

(52) U.S. Cl.
CPC ............. *A61B 8/4444* (2013.01); *A61B 8/06* (2013.01); *A61B 8/546* (2013.01); *A61B 2562/16* (2013.01)

(58) Field of Classification Search
CPC ..... A61B 2562/16; A61B 8/06; A61B 8/4444; A61B 8/546
See application file for complete search history.

(56) References Cited

U.S. PATENT DOCUMENTS

2006/0043839 A1   3/2006   Wildes et al.
2006/0086494 A1*  4/2006   Kim .................... B41J 2/471
                                                  165/185
(Continued)

FOREIGN PATENT DOCUMENTS

CN   101541378 A   9/2009
CN   101926655 A   12/2010
(Continued)

OTHER PUBLICATIONS

International Search Report dated Nov. 27, 2012 in PCT/JP12/071070 Filed Aug. 21, 2012.
(Continued)

*Primary Examiner* — Amelie R Gillman
(74) *Attorney, Agent, or Firm* — Oblon, McClelland, Maier & Neustadt, L.L.P.

(57) ABSTRACT

An ultrasound probe and ultrasonic diagnosis apparatus that can maintain surface temperature of an ultrasound probe within a safe range, without reduction in performance. The ultrasound probe includes a casing, a transducer, an electronic circuit, and a heat-transfer construction. Elements of the transducer are aligned at one end of the casing and send out ultrasound waves in accordance with their respective delay times. The electronic circuit, disposed in the casing, includes a delay circuit setting delay times and pulsers for generating pulses in accordance with the delay times, the pulses being sent to the transducer. While the electronic circuit is being energized, the heat-transfer construction disposes a member having a low heat conductivity at least either between the electronic circuit and the casing or (Continued)

between the electronic circuit and the transducer. Thereby, heat from the electronic circuit is conducted to the other end of the casing.

5 Claims, 5 Drawing Sheets

(56) References Cited

U.S. PATENT DOCUMENTS

| | | | | |
|---|---|---|---|---|
| 2006/0100513 A1* | 5/2006 | Hashimoto | ............... | A61B 8/00 600/437 |
| 2006/0186765 A1 | 8/2006 | Hashimoto | | |
| 2006/0191344 A1 | 8/2006 | Hashimoto | | |
| 2008/0294046 A1* | 11/2008 | Chiang | ................ | A61B 8/4236 600/447 |
| 2008/0306389 A1* | 12/2008 | Nagano | .................. | A61B 8/445 600/462 |
| 2010/0010350 A1 | 1/2010 | Baba et al. | | |
| 2010/0076352 A1 | 3/2010 | Kim et al. | | |
| 2010/0331702 A1 | 12/2010 | Hongou et al. | | |
| 2011/0198058 A1* | 8/2011 | Kwak | ..................... | H01L 23/34 165/104.26 |
| 2012/0143060 A1* | 6/2012 | Weekamp | ............ | G10K 11/004 600/459 |

FOREIGN PATENT DOCUMENTS

| | | |
|---|---|---|
| JP | 2005 13461 | 1/2005 |
| JP | 2006-025892 A | 2/2006 |
| JP | 2006-61696 A | 3/2006 |
| JP | 2006-102135 A | 4/2006 |
| JP | 2006-129965 A | 5/2006 |
| JP | 2007-209699 A | 8/2007 |
| JP | 2009 261840 | 11/2009 |
| JP | 2010 42244 | 2/2010 |
| JP | 2010 88610 | 4/2010 |
| WO | WO 2006/033281 A1 | 3/2006 |

OTHER PUBLICATIONS

Combined Chinese Office Action and Search Report dated Aug. 12, 2015 in Patent Application No. 201280012574.X (with English translation of categories of cited documents).

* cited by examiner

ULTRASOUND PROBE THAT EXHAUSTS HEAT VIA INFRARED-RADIATIVE HEAT TRANSFER

TECHNICAL FIELD

Embodiments of the present invention relate to ultrasound probes and ultrasonic diagnosis apparatuses.

BACKGROUND ART

In ultrasound probes used with ultrasonic diagnosis apparatuses for acquiring two- or three-dimensional images, transducer elements, which send and receive ultrasound waves, are arranged in one or two dimensions at the head part of the probe near one end side of a casing. Additionally, a group of electronic circuit cards, which are sometimes called simply "electronic circuits", are provided in the same casing, for example, to execute beam forming for driving the transducer elements.

For acquiring images in higher definition, attempts are being made to improve the electronic circuits with more functions in higher power and higher density. Consequently, the electronic circuits have come to generate more heat resulting in increased surface temperatures for the head part and the casing. Thus, effective releasing of heat from the ultrasound probe has become an important issue.

The natural cooling by the ambient air of the surfaces of the head part and the casing, however, cannot sufficiently prevent the temperature rise, and the surface temperatures tend to rise in correspondence to the time of use of the ultrasound probe.

The surface of the head part is the part that comes into contact with the subject, and the surface of the casing is the part that is held by the operator (as handle part). It is, therefore, necessary to keep the surface temperatures of the head part and handle part within a safe range.

On this background, consideration is given to a forced cooling in which a coolant is circulated through the casing via a probe cable, which extends from the other end of the casing outward, for preventing the surface temperatures from exceeding a permissible level.

PRIOR ART REFERENCES

Patent References

[Patent Reference 1] Japanese Laid-Open Patent Publication No. 2010-42244

SUMMARY OF THE INVENTION

Problems to be Solved by the Invention

There is, however, a possibility of problem that the surface temperature may not be kept in a safe range because of a drop in cooling ability, which can be caused by accidental coolant leakage out of the probe cable or by breakdown of the coolant-circulation pump.

On the other hand, in the case of natural cooling where heat is released directly through the surface of the ultrasound probe, i.e., without the use of such a coolant circulation as described above, the issue is that either the probe cannot be used continuously for a long period of time or its performance must be reduced to limit the consumed electrical power.

The embodiment is to solve the above-mentioned problems, and it is aimed for providing an ultrasound probe and an ultrasonic diagnosis apparatus capable of maintaining the surface temperature of the ultrasound probe within a safe range, without any resultant reduction in performance.

Means for Solving the Problems

To solve the above-mentioned problems, an ultrasound probe as embodiment of the present invention comprises a casing, a transducer, an electronic circuit, and a heat-transfer construction. The elements of the transducer are aligned at one end of the casing for generation of ultrasound waves in accordance with their respective delay times. The electronic circuit, which is accommodated in the casing, comprises delay circuits for setting up the respective delay times and pulsers for outputting, to the transducer elements, pulses that are generated respectively based on the delay times. The heat-transfer construction includes a member of low thermal conductivity, which is disposed at least either between the electronic circuit and the casing or between the electronic circuit and the transducer, while the electronic circuit is being electrically energized. This construction helps to transfer the heat generated by the electronic circuit to the other end of the casing.

PREFERRED EMBODIMENTS OF THE INVENTION

First Embodiment

Figure 1:
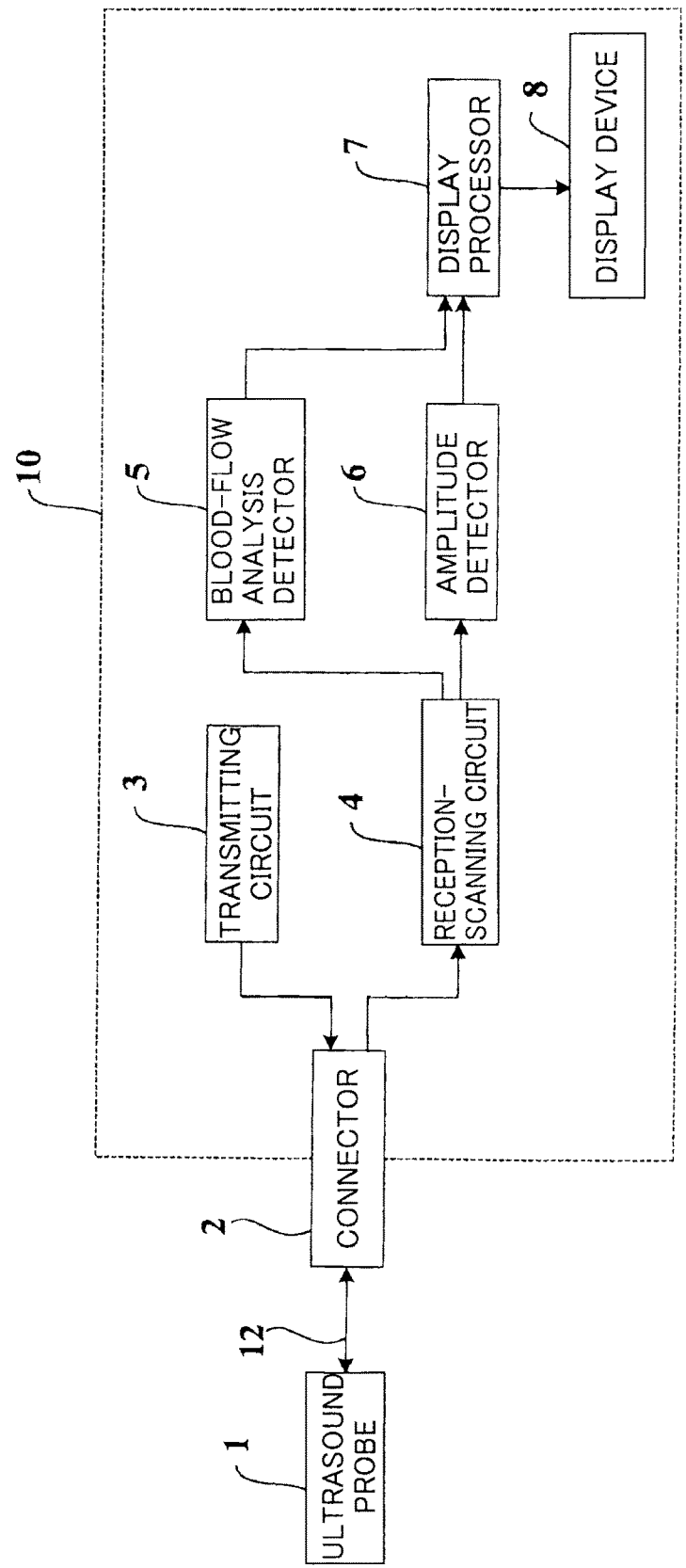
FIG. 1 is a block diagram showing the basic configuration of an ultrasonic diagnosis apparatus as a first embodiment.
Figure 2:
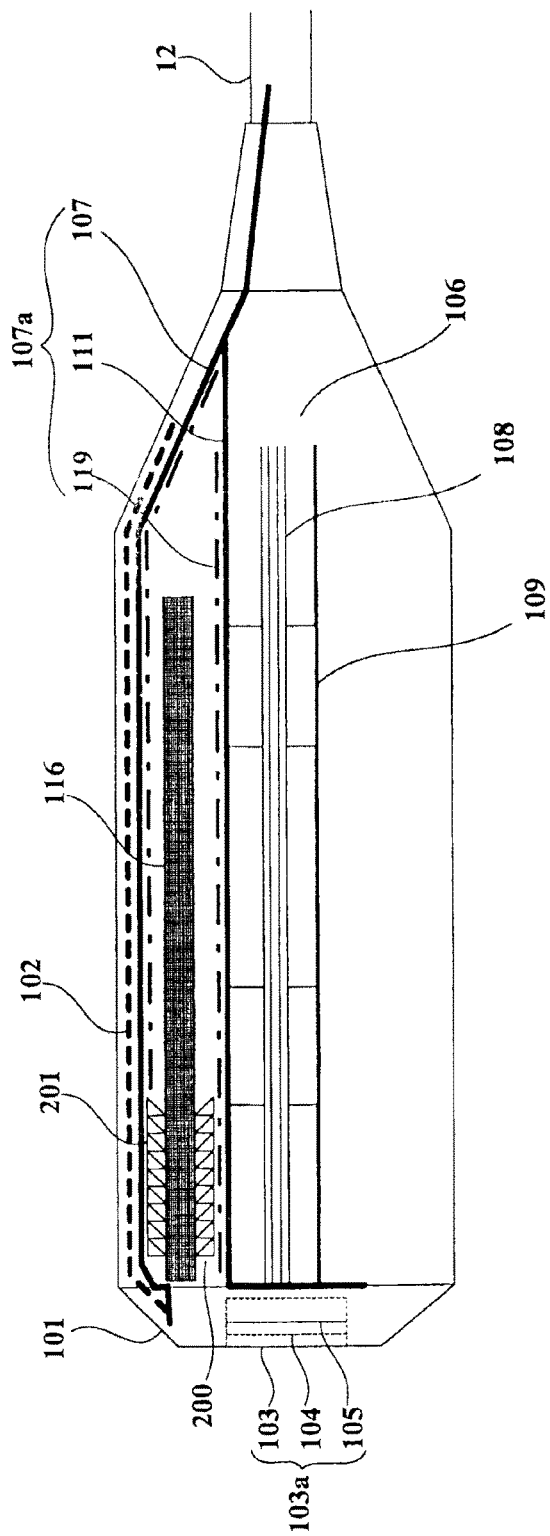
FIG. 2 is a drawing showing the internal configuration of an ultrasound probe.

Now, an ultrasound probe as a first embodiment according to the present invention and an ultrasonic diagnosis apparatus used with the ultrasound probe are explained with reference to FIGS. 1 and 2. FIG. 1 is a block diagram showing the basic configuration of the ultrasonic diagnosis apparatus, and FIG. 2 is a drawing showing the internal configuration of the ultrasound probe.

<Basic Configuration of the Ultrasonic Diagnosis Apparatus>

Figure 3:
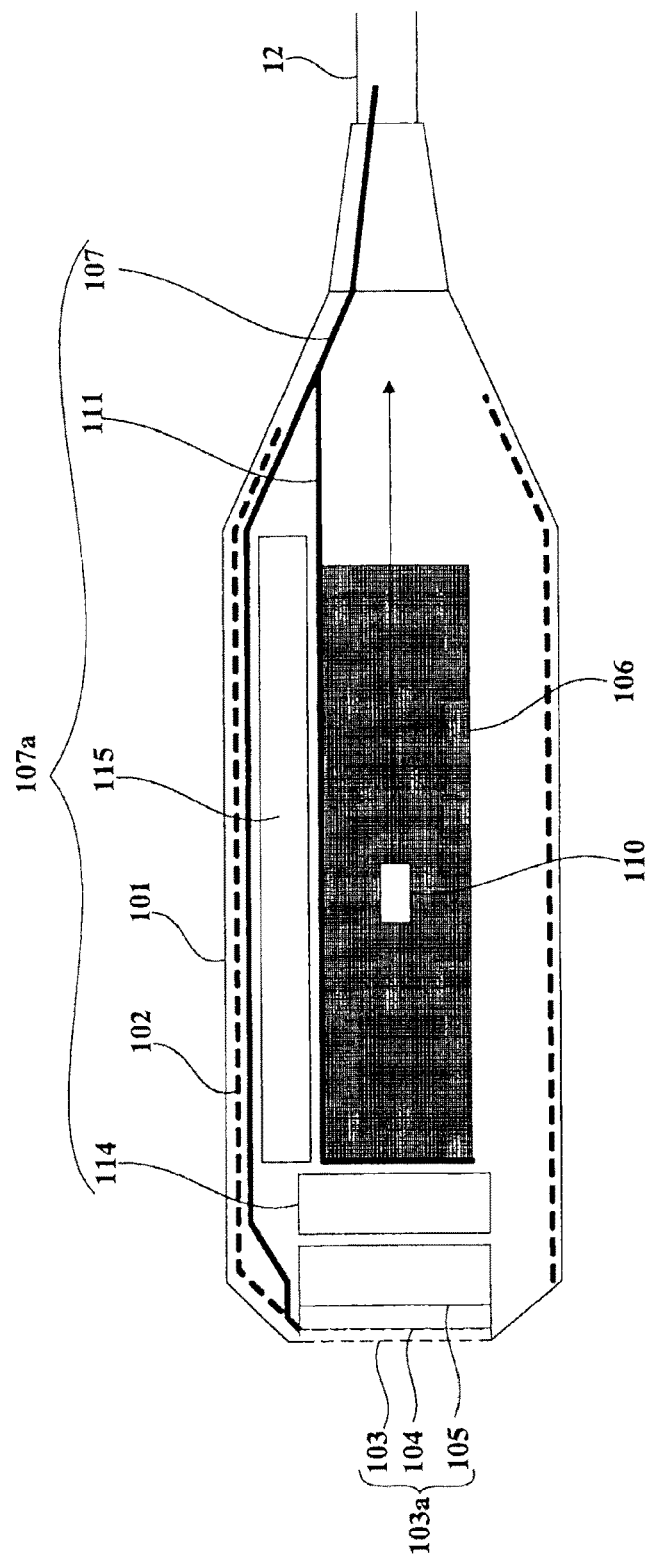
FIG. 3 is a drawing showing the internal configuration of an ultrasound probe as a second embodiment.

As shown in FIG. 1 and FIG. 3, the ultrasound probe 1 is connected to the main body 10 of the apparatus with a probe cable 12 and connector 2. The ultrasound probe 1 comprises an array of transducer elements 104, i.e., a plurality of transducer elements that interconvert acoustic signal and electric signal, enabling electronically high-speed scanning of interior organs of the subject by ultrasound wave.

The ultrasound probe 1 comprises a transducer 104 and part of a transmitting circuit 3 (a transmission-delay circuit (not shown) and pulsers (not shown)). The part of the transmitting circuit 3 provided within the ultrasound probe 1 is herein also referred to simply as "electronic circuit".

The apparatus main body 10 comprises part of the transmitting circuit 3 (a clock generator (not shown) and a frequency divider (not shown)), a reception-scanning circuit 4, a blood-flow analysis detector 5, an amplitude detector 6, a display processor 7, and a display device 8.

(Transmitting Circuit)

The transmitting circuit 3 lowers the frequency of the clock pulse generated by the clock generator, for example, to about 5 kHz rate pulse with the frequency divider and provides this rate pulse through the transmission-delay circuit to the pulsers, which in turn generate a high frequency voltage pulse to drive the transducer elements 104. In other words, the transducer is vibrated mechanically. The ultrasound waves thus generated are sent out and reflected at the boundaries of acoustic impedances inside the subject, and reflected waves are picked up by the ultrasound probe 1, the returning ultrasound waves also vibrating mechanically the transducer elements 104. By the vibration, electrical signals are generated in the transducer elements 104, individually. All these electrical signals are amplified, phased and added by the reception-scanning circuit 4 for producing signals having directionality (echo signals).

(Amplitude Detector)

Based on the echo signals from the reception-scanning circuit 4, the amplitude detector 6 generates B-mode image data providing morphological information of the tissues, and the display processor 7 performs sectional display of morphological images of the tissues, based on the B-mode image data, which have been generated by the amplitude detector 6.

(Blood-Flow Analysis Detector)

The blood-flow analysis detector 5 is a unit for realizing so-called colored Doppler imaging (CDI) and is at first configured to detect the echo signals coming from the reception-scanning circuit 4 in quadrature phase for extracting Doppler signals, which are signals that have experienced frequency shift. The analysis detector then makes only the components having a particular frequency of the extracted Doppler signals pass through an MTI filter and calculates the frequency of the signals that have passed through, with an autocorrelator. The analysis detector eventually calculates from this frequency the average velocity, distribution, and power of the blood flow with its processing unit.

Additionally, by adjustment to the passing band of the MTI filter, the blood-flow analysis detector can be switched in function between general Doppler mode, which visualizes mainly the blood flow (image data in this mode are referred to as "blood-flow Doppler image data") and tissue Doppler mode, which visualizes mainly such organs as myocardium (image data in this mode are referred to as "tissue Doppler image data").

(Display Processor and Display Device)

The display processor 7 combines the blood-flow Doppler image data and the tissue-morphological image data, which have been generated by the blood-flow analysis detector 5 described above, and displays a composition image. This image composed of tissue-morphological image data and functional image data is displayed on the display device 8.

<Configuration of the Ultrasound Probe>

Now, the configuration of an ultrasound probe as a first embodiment is described with reference to FIG. 2.

As shown in FIG. 2, the ultrasound probe 1 comprises a casing 101, a shielding member 102, an acoustic unit 103a, an electronic circuit 106, and a heat-transfer construction 107a. FIG. 2 shows only part of the electronic circuit 106.

(Casing)

The casing 101 is formed from a resin having low thermal conductivity. The surface of the casing 101 is also referred to as "handle part", since the operator holds the probe by this part.

(Shielding Member)

The shielding member 102 is disposed on the internal surface of the casing 101. The shielding member 102 is to reduce electromagnetic wave radiation and is made of such materials as copper, which is effective in electromagnetic shielding, in a form of mesh or grating to reduce its weight.

[Acoustic Unit]

The acoustic unit 103a is provided at a head part of the casing 101, the head part being one end of the casing where the acoustic unit 103a comprises a lens member 103, a transducer 104, and a backing member 105. The acoustic unit 103a is a heat-generating source.

(Transducers)

The transducer 104 sends out and receives ultrasound waves, which are created by acoustoelectric transduction. In general, the transducer 104 is an array of processed pieces of a piezoelectric material.

(Backing Member)

The backing member 105 is disposed in back of the transducer 104 to assist effective acoustic emission and reception.

(Lens Member)

The lens member 103, which functions as acoustic lens, is disposed in front of the transducer 104 (on the side opposite to the backing member 105) also for the purpose of improving the contact of the probe with the living body. By the way, the surface of the lens member 103 is the surface of the head part that comes into contact with the body surface of the subject.

(Electronic Circuit)

The electronic circuit 106, which includes part of the transmitting circuit 3 (transmission-delay circuits and pulsers), is provided in the casing 101 of the ultrasound probe 1. The electronic circuit 106 comprises a board 108 and components 109 mounted on the board, and the board 108 and the board-mounted components 109 are heat-generating sources.

[Heat-Transfer Construction]

The heat-transfer construction 107a comprises a thermal diffusion member 107, a circuit-heat transfer member 111, and a thermal radiation member 119.

(Thermal Diffusion Member)

The thermal diffusion member 107 is disposed along the shielding member 102, extending from one end of the casing 101 (the head part of the ultrasound probe 1) to the other end of the casing 101 (the tail part of the ultrasound probe 1). The thermal diffusion member plays the role of conducting the heat generated by the acoustic unit 103a (the lens member 103, the transducer 104, and the backing member 105) during ultrasonic radiation. to the tail part of the ultrasound probe 1.

The thermal diffusion member 107 may be made of a material that is effective in electromagnetic shielding, or it can be made to play a role in shielding as the shielding member 102 does, by grounding it.

(Circuit-Heat Transfer Member)

The circuit-heat transfer member 111 is disposed to envelope the electronic circuit 106, and thereby it captures and transfers the heat generated by the electronic circuit 106 to the thermal diffusion member 107 (to the tail part of the ultrasound probe 1).

(Thermal Radiation Member)

Now, the heat-transfer construction 107a is explained. In the following discussion, the heat-transfer construction 107a, which realizes heat transfer between the electronic circuit 106 and the casing 101, is described as an exemplary embodiment while no description is given of the heat-transfer construction 107a realizing heat transfer between the electronic circuit 106 and the transducer 104.

The heat-transfer construction 107a has a construction that autonomously changes its thermal conductivity in response to temperature changes, with inclusion of a thermal radiation member 119, which has a characteristic of temperature-induced infrared radiation.

The thermal radiation member 119 is equivalent to a heat transfer member that transfers heat from the electronic circuit 106 to the other end of the casing 101. It is preferable that the thermal radiation member 119 be a member that transfers heat not only in the lengthwise direction but also in the lateral direction. More preferably, the thermal radiation member be, for example, of a graphite sheet, i.e., graphite processed into a sheet. The thermal radiation member 119 of graphite sheet is capable of providing anisotropic thermal conductivity and has low thermal conductivity in the depth-wise direction of the sheet but high thermal conductivity along the surface of the sheet. As a result, the thermal radiation member 119 transfers heat from the electronic circuit 106 easily along the surface of the sheet (to the other end of the casing 101). On the other hand, the thermal radiation member 119 scarcely transfers heat from the electronic circuit 106 in the depth-wise direction of the sheet (toward the casing). The thermal radiation member 119 may be provided in mesh or with slits, and also be made to play a shielding role as the shielding member 102, by grounding it, or it may be made to play the same role as the thermal diffusion member 107.

As shown in FIG. 2, the thermal radiation member 119 is laid on the circuit-heat transfer member 111 and is so energized by the heat of the circuit-heat transfer member 111 that the thermal radiation member emit infrared rays toward a heat-receiving member 116, which extends to the other end of the casing 101 (to the tail part of the ultrasound probe 1).

The thermal radiation member 119 is disposed also along the thermal diffusion member 107 and is energized also by the heat of the thermal diffusion member 107, emitting infrared rays toward the heat-receiving member 116.

By the characteristic of temperature-induced radiation, as the temperatures of the electronic circuit 106 and the circuit-heat transfer member 111 rise, the radiant energy of the thermal radiation member 119, which has a high infrared emissivity, increases exponentially by the fourth power of the surface temperature T. In contrast with general heat conduction, where the energy being conducted increases in proportion to the temperature difference, in thermal radiation, the energy being transmitted increases explosively at high temperatures. The thermal radiation, therefore, is equivalent to as if a heat conduction were performed with an increasing rate of thermal conductivity.

For example, between 35 degrees Celsius (273+35=308 deg. K) and 60 degrees Celsius (273+60=333 deg. K), while a general heat transfer presents an 8% increase ($\approx(333-308)/308\times100$) in conducted energy, a thermal radiation presents a 36% increase ($\approx(1.08^4-1)\times100$). Even in a case of abnormal temperature rise, this characteristic of thermal radiation is effective in autonomously raising the thermal conductivity.

As shown in FIG. 2, the first embodiment, furthermore, comprises infrared-refracting prisms 200 on the surface of the thermal radiation member 119 especially inside the part of the casing 101 of the ultrasound probe 1 by which the operator holds the probe, where a rise in temperature should be avoided. The infrared-refracting prisms 200 refract the radiation coming toward the part which directly faces the surface of the thermal radiation member 119, i.e., the part whose temperature rise should be avoided (toward the surface of the casing 101). This refraction directs the radiation to the tail part of the ultrasound probe 1 (in the direction of the other end of the casing 101), which is the upper right area in FIG. 2. Likewise, on the surface of the heat-receiving member 116 at the area where temperature rise should be avoided, infrared reflectors 201 are juxtaposed to reflect and slant infrared rays (in the direction of the other end of the casing 101). The infrared-refracting prisms 200 and the infrared reflectors 201 together work to reduce radiant heat absorption in this area.

(Connector Part and Probe Cable)

One end of the probe cable 12 is connected to the tail part of the ultrasound probe 1 (the other end of the casing 101, i.e., the end opposite to the transducer 104) while the other end of the probe cable 12 is connected to the apparatus main body 10 with connector parts (not shown). The probe cable 12 is a composite cable that comprises a signal line to conduct electrical signals and a power line to supply electrical power.

In the first embodiment, which has been described above, since the probe employs a construction whose thermal conductivity autonomously changes in correspondence to the change in temperature of the electronic circuit 106, the probe is capable of autonomously raising its thermal conductivity even in a case of abnormal temperature rise.

In other words, although the first embodiment does not provide active temperature control, it realizes an improvement in heat transfer efficiency during temperature rise, with a relatively simple construction. The first embodiment, thereby, realizes a limit to the temperature rise caused by the heat generated by the electronic circuit 106.

Second Embodiment

Figure 4:
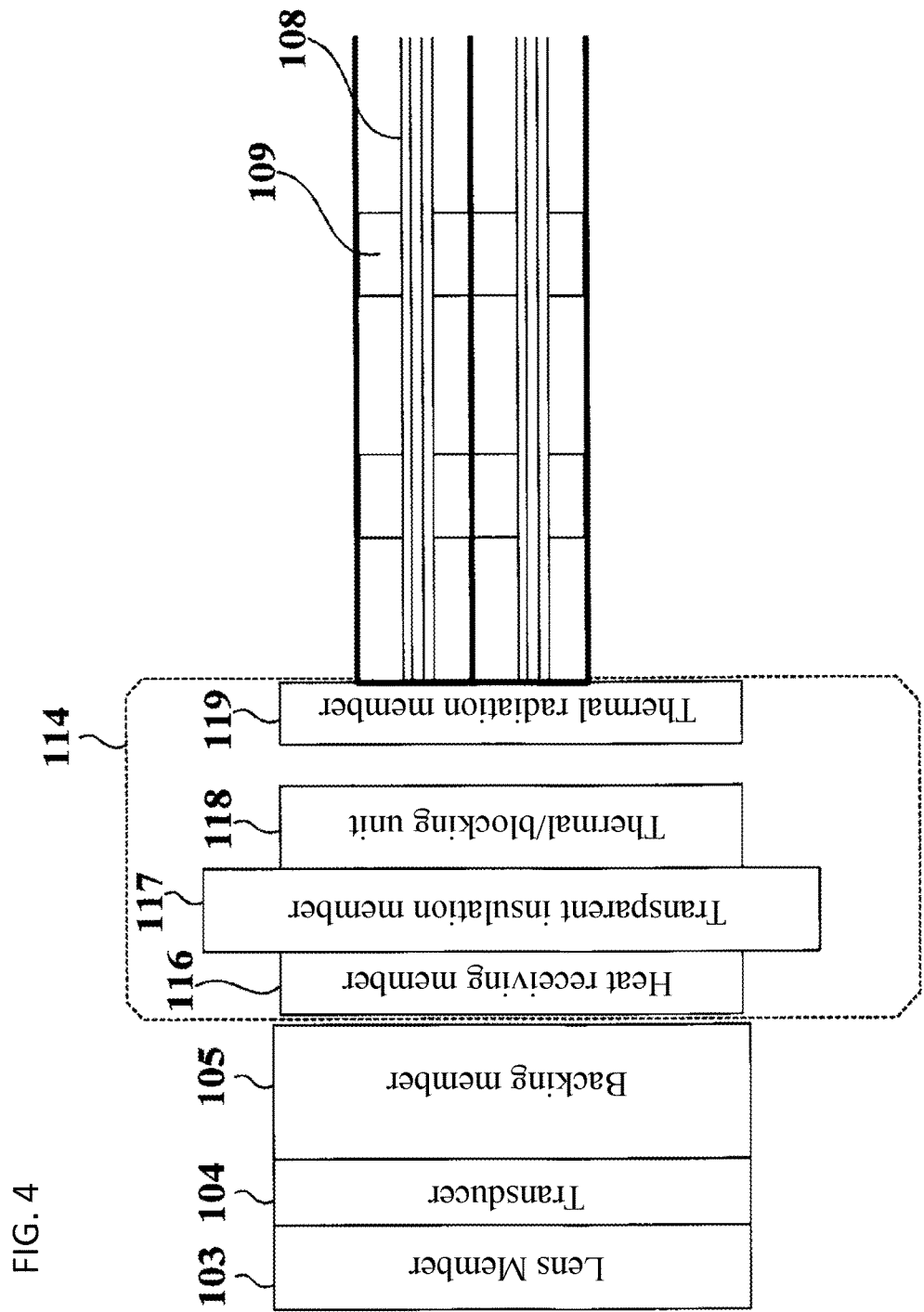
FIG. 4 is a drawing showing the construction of a thermal conductivity modification unit.

Now, an ultrasound probe as a second embodiment is described with reference to FIGS. 3 and 4. FIG. 3 is a drawing showing the internal configuration of the ultrasound probe, and FIG. 4 is a drawing showing the configuration of a thermal conductivity modification unit.

The heat-transfer construction 107a in the first embodiment comprises the thermal radiation member 119 as described above, but the heat-transfer construction 107a in the second embodiment comprises thermal conductivity modification unit 114, 115, instead of the thermal radiation member 119.

In the following description of the configuration of the second embodiment, the parts that are duplicated from those in the first embodiment are given the same reference numerals as in the first embodiment, and their description is omitted here.

[Heat-Transfer Construction]

The heat-transfer construction 107a comprises a thermal diffusion member 107, a circuit-heat transfer member 111, and thermal conductivity modification unit 114, 115.

(Heat-Conductivity Modification Unit)

As shown in FIG. 3, one of the thermal conductivity modification unit 114 is disposed between the acoustic unit 103a (backing member 105) and the electronic circuit 106 and reduces transmission of the heat generated by the electronic circuit 106 to the acoustic unit 103a. This thermal conductivity modification unit 114, thereby, restricts temperature rise on the surface of the lens member 103 (the surface of the head part), which might be caused otherwise by the heat from the electronic circuit 106.

The other of the thermal conductivity modification unit 115 is provided between the circuit-heat transfer member 111 and the thermal diffusion member 107 or shielding member 102. This thermal conductivity modification unit is configured to prevent direct transmission of heat from the circuit-heat transfer member 111 to the thermal diffusion member 107 or to the shielding member 102. The thermal conductivity modification unit 115 can prevent local temperature rise near the electrical circuit in the casing 101 of the ultrasound probe 1.

Since the temperature inside the casing 101 tends to rise higher than conventional models, the electronic circuit 106 needs to be designed to function at a higher temperature. If the operational mode, particularly, involves consumption of much more electrical power continually for an extended time, then the internal temperature can increase close to a critical point. Even in a case where the scanning has stopped because of the switching of the operational mode into still-image display or where the power consumption of the electronic circuit 106 in the casing 101 has dropped because of the selection of another ultrasound probe 1, due to the effect of the insulation member, if the heat transmission is normal, then the rate of temperature decrease at the electronic circuit 106 is slow. In this case, later when the operational mode requiring much more power consumption is resumed, the temperature of the electronic circuit 106 will not have sufficiently decreased yet, and the temperature rise will restart from a higher temperature.

To solve this kind of problem, the thermal conductivity modification unit 115 is configured to modify its thermal conductivity for the purpose of accelerating the rate of temperature decrease at the electronic circuit 106 when the power consumption of the electronic circuit 106 has dropped.

In this way, the temperature can be sufficiently lowered by the time when the operational mode requiring much more power consumption is resumed. The lime required of the internal temperature to rise close to a critical point is consequently lengthened. This can allow more electrical power consumption.

Now, the details of the thermal conductivity modification unit are described with reference to FIG. 4, which is a drawing showing the configuration of the thermal conductivity modification unit.

The thermal conductivity modification unit 114 and 115 do have the same construction, so in the following description, one of the thermal conductivity modification unit 114 is described as the exemplary, and the description of the other thermal conductivity modification unit 115 is omitted.

As shown in FIG. 4, the thermal conductivity modification unit 114 comprises a thermal radiation member 119, which has a high infrared emissivity, an infrared transmitting/blocking unit 118, which transmits or blocks infrared rays, a transparent insulation member 117, which lets infrared rays pass through and has a low thermal conductivity, and a heat-receiving member 116, which has a high infrared emissivity.

(Thermal Radiation Member)

The thermal radiation member 119 is connected with a circuit-heat transfer member 111 at a low thermal resistance. The thermal radiation member 119 has a high emissivity (more than 0.95) achieved by coating the surface of such a material as copper foil, which has a high thermal conductivity, with a ceramic material. The thermal radiation member is disposed facing its ceramic-coated surface toward the heat-receiving member 116. As the thermal radiation member 119 receives heat transmitted from the circuit-heat transfer member 111, the heat accumulating raises the temperature of the radiation member. This thermal energy increase makes the ceramic-coated surface emit far-infrared rays in the direction of the heat-receiving member 116, resulting in an energy transfer. In this arrangement, the thermal radiation member 119 and the heat-receiving member 116 constitute an infrared transmitter, which transmits infrared rays.

(Heat-Receiving Member)

The heat-receiving member 116 is connected with the backing member 105 at a low thermal resistance. The heat-receiving member 116 has a high emissivity (more than 0.95) achieved by coating the surface of such a material as copper foil, which has a high thermal conductivity, with a ceramic material. The heat-receiving member is disposed facing its ceramic-coated surface toward the thermal radiation member 119.

(Transparent Insulation Member)

The transparent insulation member 117 is formed of a material having a low thermal conductivity but capable of letting far-infrared rays pass through. The transparent insulation member 117 is disposed between the infrared transmitting/blocking unit 118 and the heat-receiving member 116.

The transparent insulation member 117 is preferably made of a material that includes air whose convection is suppressed, for adiathermancy and lightness. This material may be an air-bubble cushioning material made of a thin polyethylene film, which is used as a cushioning material for packing. This member may also be appropriately made of thin multiple sheets of glass (air sandwiched between the two glass plates). Polyethylene and glass do not themselves have high infrared transmittance, but if they are made into a thin film, then their transmittance is sufficient (more than 90%). Paper like shoji paper is not suitable since it is not easily made into a thin film and gives much reflection, with only about 50% transmittance, though it is effective for preventing air convection.

(Infrared Transmitting/Blocking Unit)

The infrared transmitting/blocking unit 118 comprises, for example, a liquid crystal shutter. It is preferable that the liquid crystal shutter have high infrared transmittance rather than low infrared transmittance, the latter being the case, for example, in those used for visible rays. An example of the liquid crystal shutter is mentioned in Japanese Patent Application No. H5-129714. Silicon plates are employed as infrared transmission plates and endowed with a parallel arrangement of lattice electrodes of gold so as to function as polarizing plates. The gold electrodes are, furthermore, made to function as orientation film and filled with a liquid crystal material while their polarization directions are set at right angles to block the transmission of infrared rays.

If the controller (not shown) determines that the electronic circuit 106 is not supplied with power and/or that the temperature of the electronic circuit 106 has risen beyond a predetermined value, the controller supplies electric power to the infrared transmitting/blocking unit 118 in order to open the infrared transmitting/blocking unit 118 for transmitting infrared rays. On the other hand, if the controller determines that the electronic circuit 106 is being supplied with power and that the temperature of the electronic circuit 106 is equal to or below the predetermined value, the controller cuts oil the power supply to the infrared transmitting/blocking unit 118 in order to close the infrared transmitting/blocking unit 118 for blocking infrared rays.

The directions of polarization of the liquid-crystal polarizing plates in the infrared transmitting/blocking unit 118 are controlled such that infrared rays are blocked while power is supplied to the electronic circuit, and that infrared rays are transmitted while power is not supplied. On the one hand, when the infrared transmitting/blocking unit 118 transmits infrared rays, the thermal conductivity of the heat-transfer construction is enhanced between the circuit-heat transfer member 111 and the acoustic unit 103a. On the other hand, when the Infrared transmitting/blocking unit 118 blocks infrared rays, the thermal conductivity is lowered therebetween.

While the electronic circuit 106 is not electrically energized, the infrared transmitting/blocking unit 118 is open. In this state, the far-infrared rays emitted from the thermal radiation member 119 pass through the infrared transmitting/blocking unit 118 and the transparent insulation member 117, and the heat-receiving member 116 is, thus, irradiated by the far-infrared rays, which are converted into heat in the heat-receiving member 116. Through this far-infrared transmission, the heat from the circuit-heat transfer member 111 is transferred to the backing member 105, and the heat is further transmitted to the transducer 104, and through the lens member 103 into the ambient air.

When the electronic circuit 106 is energized, the infrared transmitting/blocking unit 118 is closed. In this state, the far-infrared rays emitted from the thermal radiation member 119 are absorbed or reflected by the infrared transmitting/blocking unit 118 and do not reach the acoustic unit 103a (the lens member 103, the transducer 104, and the backing member 105). The reflected far-infrared rays fall on the thermal radiation member 119 and return into heat energy. The heat absorbed by the infrared transmitting/blocking unit 118 raises the temperature of the infrared transmitting/blocking unit 118, but the transmission of heat to the acoustic unit 103a is prevented by the transparent insulation member 117.

[Actions]

Now, the actions of the ultrasound probe as a second embodiment are explained.

The generation of ultrasound waves by the ultrasound probe 1 is realized by application of electrical pulse to the transducer 104, which produces mechanical vibration. Because of an energy loss encountered during this electromechanical transduction, heat is generated in the transducer 104. Moreover, the generated vibration reaches the lens member 103 and the backing member 105. As the acoustic energy is transmitted to the backing member 105, acoustic energy decrease is converted into heat. The acoustic energy transmitted to the lens member 103 passes through the lens member 103 and into the subject. The acoustic energy passing through the lens member 103 attenuates while partially converted into heat energy.

The surface of the lens member 103 (the surface of the head part) of the ultrasound probe 1 shown in FIG. 3 is kept in contact with the body surface of the subject during examination, so any temperature rise at the surface, therefore, is a great safety concern. It is important to restrict the temperature rise at the surface of the lens member 103. For the purpose of diffusing the heat around the backing member 105 and the transducer 104 and of preventing radiowave transmission, the shielding member 102 is connected to the transducer 104, in addition, the backing member 105 is embedded with a temperature sensor (not shown), whose signal is sent to the apparatus main body 10 through a line for temperature detection (not shown). The apparatus main body 10 is configured to detect any abnormal temperature rise at the surface of the lens member 103 by determining the signal from the sensor.

In the non-electrification state where the ultrasound probe 1 attached to the system is not used for diagnostic image acquiring, there is little power consumption by the circuit in the ultrasound probe 1, and also no power is supplied to the transducer 104. As a result, there is no temperature rise either at the surface of the lens member 103 (the surface of the head part) or at the surface of the casing 101 (the surface of the handle part). In addition, in the non-electrification state, the infrared transmitting/blocking unit 118 is set to allow infrared ray transmission. However, since the internal temperature is the same as the ambient air, and the temperature of the thermal radiation member 119 and the circuit-heat transfer member 111 is equal to the temperature of the heat-receiving member 116 and the backing member 105, there is no heat transmission by radiation.

When an ultrasound probe 1 to be employed is selected and a diagnostic image acquiring is initiated, the infrared transmitting/blocking unit 118 is set into its blocking state before electric power is supplied for ultrasound transmission and reception. The electrical power applied in this state of electrification differs depending on the type, the target range, and the imaging mode of the ultrasound probe 1. It is, however, approximately 1 W-3 W, which can start a temperature rise at the surface of the electronic circuit 106. This temperature rise affects the circuit-heat transfer member 111, and through the thermal diffusion member 107 or the shielding member 102, reaches the casing 101 of the ultrasound probe 1, resulting in a temperature raise at the casing. Although the casing 101 of the ultrasound probe 1 is cooled by the ambient air, the temperature continues rising gradually. Since the surface of the lens member 103 is insulated against a heat from the electronic circuit 106, only a temperature rise due to the transducer 104 generating ultrasonic energy is observable. This temperature rise is approximately equal to that observable in the case where the electronic circuit 106 were not integrated in the ultrasound probe 1. In this condition, ultrasonic energy can be generated sufficiently to acquire various tomographic images.

After having acquired images necessary for a diagnosis, the operator halts (freezes) the image acquiring on this occasion, and analyzes and/or records the image information so far stored in the system.

When this image acquiring is stopped, the infrared transmitting/blocking unit 118 is switched into its transmission state. This state expedites temperature drop at the electronic circuit 106, whose power consumption has been reduced, now generating little heat. In this condition, no heat is generated from the transducer 104, which is not currently in ultrasonic energy generation. Even if heat is transferred through the thermal conductivity modification unit 115, the temperature rise that may occur at the surface of the lens member 103 is no threat to the safety.

It is possible to add to the probe a function to observe the temperature around the electronic circuit 106 by providing a circuit temperature sensor 110. In this case, if the temperature around the electronic circuit 106 rises beyond a predetermined value (e.g. the temperature exceeding the operational range of the board-mounted components 109, or rising closer to a critical temperature at which some components may experience irreversible breakdown including damage to their long-term reliability), then the power consumption of the electronic circuit 106 may be reduced or terminated as protection measure. In addition to that, heat transfer is enhanced by the thermal conductivity modification unit 114, 115, which expedite the lowering of the temperature of the electronic circuit 106. As a result, the utility and reliability of the probe is improved.

Modified Embodiments

Embodiments are not limited to those described above. Those embodiments can be implemented in various modifications.

For example, the infrared transmitting/blocking unit 118 may comprise not only a liquid crystal shutter but also a means of mechanically rotating an optically blocking plate. In this case, a mechanism comprising a spring for setting up an initial state is effective in returning the probe, even after power cut-off, into the state that allows infrared ray transmission.

The thermal conductivity modification unit 114, 115 may comprise not only a shutter that blocks infrared ray transmission but also a fluid circulation that can be stopped circulating. It may also be an insulation mechanism whose thermal conductivity changes with its phase change from solid to liquid, which can then circulate, in response to temperature change. It may also be an insulation mechanism that incorporates a shape-memory metal that transforms in response to temperature change.

For facilitating heat transfer to the probe cable 12 inside the casing 101, such materials as copper sheets, copper foil, carbon sheets, and heat pipes may be used along with a small compressor.

The above-mentioned embodiments of ultrasound probe 1 are described with a cooling system in which the probe cable 12 does not include a coolant in circulation. It however, possible to realize an ultrasound probe 1 whose probe cable 12 includes a coolant in circulation.

Comparative Embodiments

Now, the internal configuration of an ultrasound probe as a comparative embodiment is described with reference to FIG. 5, which is a drawing showing the internal configuration of the ultrasound probe.

In the description of the configuration of the comparative embodiment, the parts that are duplicated from those of the first embodiment are given the same reference numerals as in the first embodiment, and their description is omitted here.

In the configuration of the comparative embodiment, the probe does not include a heat-transfer construction that plays a role of insulation between the electronic circuit 106 and the transducer 104 in the same way as the configuration of the above mentioned embodiments. In addition, the construction that facilitates heat transfer between the electronic circuit 106 and the casing 101 does not take advantage of the characteristic of temperature-induced infrared radiation.

Figure 5:
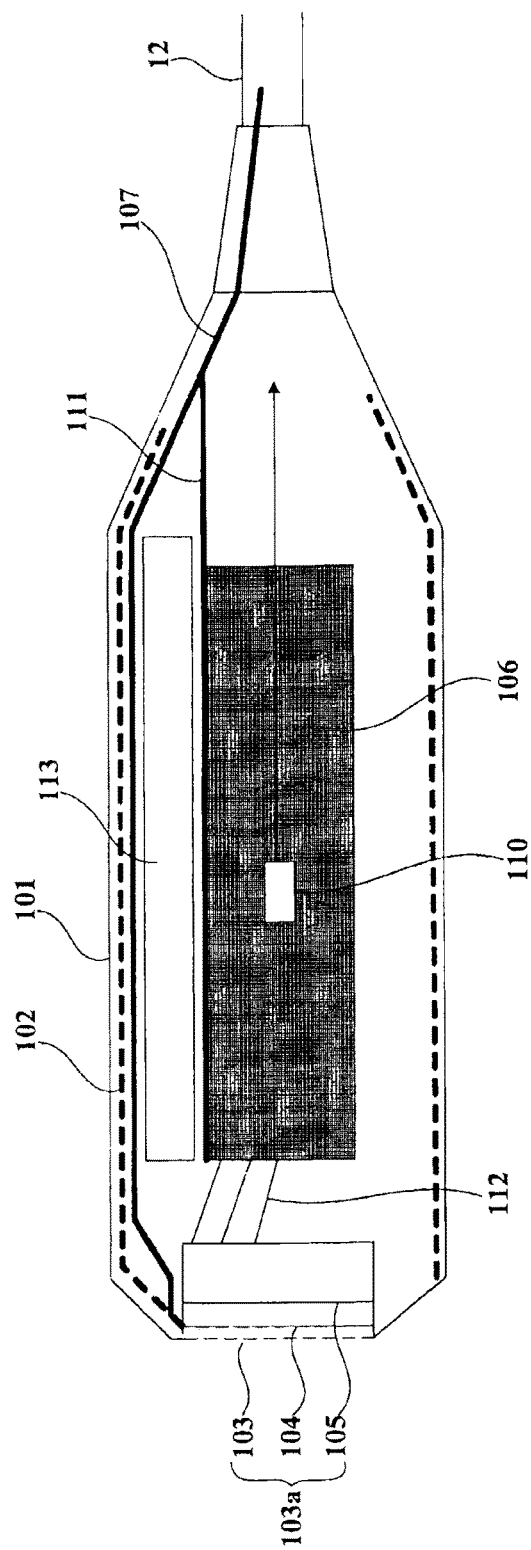
FIG. 5 is a drawing showing the internal configuration of an ultrasound probe used as a comparative embodiment.

As shown in FIG. 5, a circuit-heat transfer member 111 is provided inside the ultrasound probe 1, covering the electronic circuit 106 so that the circuit-heat transfer member 111 can conduct the heat generated by the electronic circuit 106 to the outside of the probe. More specifically, the circuit-heat transfer member 111 is connected with a thermal diffusion member 107 to transfer heat outward for realizing thermal radiation from the probe cable 12. Heat is also conducted to a shielding member 102, from which it is further led to the casing 101, where natural cooling takes place by the ambient air.

In the configuration of the comparative embodiment, a heat transfer member 113 is provided to facilitate heat transfer between the circuit-heat transfer member 111 and the thermal diffusion member 107 or the shielding member 102. In addition, the electronic circuit 106 and the transducer 104 are electrically connected for signal transmission and reception through a signal-connection flexible board 112 or a probe cable 12. In this case, the conductors used for this electrical connection and the air existing in gaps surrounding the conductors are used for conducting the heat generated by the electronic circuit 106 to the lens member 103, the transducer 104, and the backing member 105.

A circuit temperature sensor 110 is provided near the electronic circuit 106 and is connected to the apparatus main body 10, and the temperature in the vicinity of the electronic circuit 106 is monitored by a control unit (not shown), which is provided in the apparatus main body 10. Another temperature sensor (not shown) is embedded near the transducer 104, and the temperature in the vicinity of the transducer 104 is observed.

As mentioned previously, the surface of the lens member 103 comes into contact with the body surface of a patient subjected to the examination. It is, therefore, important to control the surface temperature not to rise excessively, which may otherwise be a serious safety problem. In addition, the casing 101 of the ultrasound probe 1 is the part that the operator performing examination holds with a hand. Thus, it is also important to control the temperature of this area on the probe not to rise excessively, lest the examiner get the hand burned or feel unpleasantness. The electrical power applied to the electronic circuit 106 is, therefore, limited with some restrictions on transmission energy and on biasing current applied to the receiver circuit. As a result, the probe is somewhat operated in a state that permits saturation and increased noise. In the configuration of the comparative embodiment, there has been an attempt to optimize the design by reducing the thermal resistance of the shielding member 102, but there is a limit in reducing the thermal resistance within the limited space available inside the probe. This situation makes it difficult to effectively optimize the cooling ability of the probe by means of homogenizing its surface temperature over the casing 101. In the case of such a cardiovascular ultrasound probe 1, even at a power consumption lower than 2 W, the surface temperature can sometimes reach a critical temperature in safety.

On the other hand, in the above-mentioned embodiment, the thermal conductivity of the probe is autonomously modified in correspondence to the temperature of the electronic circuit 106, and the surface temperature of the ultrasound probe 1 is kept in a safe range by the modification of the thermal conductivity, which controls heat transfer.

Some embodiments according to the present invention have been described so far. These embodiments are, however, presented only as examples, without any intention to limit the scope of the invention. The embodiments stated above are intended to apply particularly for including, in the probe, pulsers, which comprise high speed and high voltage transistors as transmitting circuit. A similar effect is, however, achievable by a configuration in which the transmitting circuit supplies high voltage pulses by pulsers that are provided in the main body, with the number of pulsers being smaller than the number of the transducer elements. In this case, the high voltage pulses are selectively supplied, with a switching circuit provided in the probe, to the individual elements in accordance with their respective delay times. While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of embodiments described herein may be made without departing from the spirit of the inventions. The accompanying claims and their equivalents are intended to cover such forms or modifications as would fall within the scope and spirit of the inventions.

DESCRIPTIONS OF NUMBERED PARTS

Numeral 1 designates an ultrasound probe; 2, connector; 3, transmitting circuit; 4, reception-scanning circuit; 5, blood-flow analysis detector; 6, amplitude detector; 7, display processor; 8, display device; 12, probe cable; 101, casing; 102, shielding member; 103, lens member; 103*a*, acoustic unit; 104, transducer; 105, backing member; 106, electronic circuit; 107*a*, heat-transfer construction; 107, thermal diffusion member; 108, board; 109, board-mounted components; 110, circuit temperature sensor; 111, circuit-beat transfer member; 112, signal-connection flexible board; 113, heat transfer member; 114, heat-conductivity modification unit; 115, heat-conductivity modification unit; 116, heat-receiving member; 117, transparent insulation member; 118, infrared transmitting/blocking unit; 119, thermal radiation member; 200, infrared-refracting prism; and 201, infrared reflector.

What is claimed is:

1. An ultrasound probe for sending and receiving ultrasound waves, comprising:
    a casing having a first end and a second end with a middle part disposed therebetween, the second end being an opposite end of the first end;
    a transducer comprising transducer elements, which are aligned at the first end of the casing and are configured, respectively, to emit ultrasound waves in accordance with delay times;
    an electronic circuit comprising a delay circuit accommodated in the casing and configured to set the delay times and a pulser configured to generate pulses based on the delay times and output, the pulses to the transducer elements; and
    a heat-transfer construction arranged between the first end and the second end of the casing, the heat-transfer construction comprising
        a thermal diffusion member accommodated in the casing, located along an inner surface of the casing and thermally contacting the second end of the casing, the inner surface corresponding to an inside of the middle part,
        a circuit-heat transfer member arranged to envelope at least a part of the electronic circuit and conduct heat from die electronic circuit, and
        a thermal-radiation member configured to convert heat received from the electronic circuit through the circuit-heat transfer member into infrared rays that are transmitted to the thermal diffusion member and an optical component in the casing, wherein
    the optical component is located between the thermal diffusion member and the thermal-radiation member and configured to reduce heating of the first end and the middle part by redirecting a part of the infrared rays that are transmitted from the thermal-radiation member towards the first end and the middle part by reflecting or refracting the part of the infrared rays toward the second end of the casing, and
    the thermal-radiation member is located at least between the electronic circuit and the casing at a distance from the optical component providing a transmission path for the infrared rays converted from the heat received through the circuit-heat transfer member.

2. An ultrasound probe according to claim 1, wherein the thermal-radiation member includes a material that has a thermal conductivity that is temperature dependent.

3. An ultrasound probe according to claim 1, wherein the thermal-radiation member is a mesh.

4. An ultrasound probe according to claim 3, wherein the thermal-radiation member a graphite sheet.

5. An ultrasonic diagnosis apparatus comprising:
    an ultrasound probe according to claim 1; and
    a main body configured to be connected to the ultrasound probe and create images based on signals received by the ultrasound probe.

* * * * *